United States Patent [19]

van Doorn et al.

[11] Patent Number: 4,933,311
[45] Date of Patent: Jun. 12, 1990

[54] POLYMERIZATION PROCESS

[75] Inventors: Johannes A. van Doorn; Richard L. Wife, both of Amsterdam, Netherlands

[73] Assignee: Shell Oil Company, Houston, Tex.

[21] Appl. No.: 343,229

[22] Filed: Apr. 26, 1989

Related U.S. Application Data

[62] Division of Ser. No. 7/208,948, Jun. 20, 1988, Pat. No. 4,877,861.

[30] Foreign Application Priority Data

Jun. 24, 1987 [NL] Netherlands ......................... 8701473

[51] Int. Cl.$^5$ ............................................. B01J 31/24
[52] U.S. Cl. .................................... 502/162; 502/170
[58] Field of Search ................................ 502/162, 170

[56] References Cited

U.S. PATENT DOCUMENTS 4,474,978 10/1984 Drent et al. .................... 502/339 X
4,855,399 8/1989 van Doorn et al. ............ 502/162 X

FOREIGN PATENT DOCUMENTS 0121965 10/1984 European Pat. Off. .
0181014 5/1986 European Pat. Off. .
0222454 5/1987 European Pat. Off. .

Primary Examiner—Patrick P. Garvin
Attorney, Agent, or Firm—Dean F. Vance

[57] ABSTRACT

In the process of producing a linear alternating polymer of carbon monoxide and at least one ethylenically unsaturated hydrocarbon in the presence of a palladium salt, the anion of a strong non-hydrohalogenic acid and a bis(phosphino)propane, improved polymerization rates are obtained when employing a novel catalyst composition formed from a novel 1,3-bis(phosphino)propane wherein the propane moiety is additionally substituted in the 2 position with two hydrocarbyl substituents.

8 Claims, No Drawings

POLYMERIZATION PROCESS

This is a division of application Ser. No. 208,948, filed June 20, 1988, and now Pat. No. 4,877,861.

FIELD OF THE INVENTION

This invention relates to an improved process for the production of linear alternating polymers of carbon monoxide and at least one ethylenically unsaturated hydrocarbon. More particularly, the invention relates to an improved process wherein the carbon monoxide and hydrocarbon(s) are contacted in the presence of a catalyst composition formed from a palladium salt, the anion of a strong non-hydrohalogenic acid and a bis(-phosphino)propane ligand wherein the propane group additionally contains two hydrocarbyl substituents in the 2 position.

BACKGROUND OF THE INVENTION

Polymers of carbon monoxide and ethylenically unsaturated hydrocarbons have been known for some time. Brubaker, U.S. Pat. No. 2,495,286, produced such polymers of relatively low carbon monoxide content in the presence of free radical initiators, e.g., peroxy compounds. U.K. No. 1,081,304 discloses the production of similar polymers of higher carbon monoxide content in the presence of alkylphosphine complexes of palladium salts as catalyst. Nozaki extended this reaction to produce linear alternating polymers in the presence of arylphosphine complexes of palladium moieties and certain inert solvents. See, for example, U.S. Pat. Nos. 3,689,460 and 3,694,412.

More recently, the class of linear alternating polymers of carbon monoxide and ethylenically unsaturated hydrocarbons has become of greater interest in part because of the greater availability of the polymers in quantity. Production of this class of polymers, also known as polyketones or polyketone polymers, is illustrated by a number of Published European Applications including 121,965 and 181,014 and by copending U.S. patent application Ser. No. 930,468 filed Nov. 14, 1986. These references illustrate the production of linear alternating polymers of carbon monoxide and ethylenically unsaturated hydrocarbons in the presence of catalyst compositions formed from a compound of palladium, cobalt or nickel, the anion of a non-hydrohalogenic acid having a pKa less than about 6 and a bidentate ligand of phosphorus, arsenic or antimony.

In general, these polymerization catalyst compositions preferably are formed, inter alia, from a bidentate ligand of phosphorus, particularly a bis(phosphino)alkane, and best results are obtained when the catalyst composition is formed from a 1,3-bis(phosphino)propane. Phosphine ligands such as 1,3-bis(diphenylphosphino)propane and 1,3-bis[di(2-methoxyphenyl)-phosphino]propane are illustrative of this class of preferred bis-(phosphino)propanes. While these catalyst compositions are efficient in catalyzing the production of the linear alternating polymers, it would be of advantage to provide even more active catalyst compositions.

SUMMARY OF THE INVENTION

This invention relates to an improved process of producing linear alternating polymers of carbon monoxide and at least one ethylenically unsaturated hydrocarbon, as well as to the catalyst composition employed in such production and to certain novel bis(phosphino)propanes employed in the catalyst compositions. More particularly, the invention relates to the production of such linear alternating polymers in the presence of a catalyst composition formed from a palladium salt, the anion of a strong non-hydrohalogenic acid and a bidentate ligand of phosphorus wherein the ligand is a 1,3-bis(phosphino)propane in which the propane moiety has two additional hydrocarbyl substituents in the 2 position. The use of such catalyst compositions and phosphine ligands results in an improved rate of polymerization.

DESCRIPTION OF THE INVENTION

In the process of the invention, linear alternating polymers of carbon monoxide and at least one ethylenically unsaturated hydrocarbon are produced by contacting the carbon monoxide and hydrocarbon(s) in the presence of a catalyst composition formed from a palladium compound, the anion of a non-hydrohalogenic acid having a pKa below about 6 and a bidentate ligand of defined structure.

The palladium compound precursor of the catalyst compositions is the salt of palladium and an acid, organic or inorganic. The palladium salt is preferably a palladium carboxylate, especially the palladium salt of a mono- or dicarboxylic acid. The preferred palladium carboxylates are palladium alkanoates of up to about 10 carbon atoms. While palladium alkanoates such as palladium propionate, palladium butyrate or palladium octanoate are usefully employed in the process of the invention, the preferred palladium alkanoate is palladium acetate.

The anion precursor of the catalyst composition of the invention is the anion of a non-hydrohalogenic acid having a pKa below about 6 and preferably below about 2, as determined in aqueous solution at 18° C. Preferred anions are anions of oxygen-containing acids including anions of inorganic acids such as sulfuric acid, perchloric acid, phosphoric acid and nitrous acid as well as organic acids including sulfonic acids such as p-toluenesulfonic acid, trifluoromethanesulfonic acid, 2-hydroxypropane-2-sulfonic acid and methanesulfonic acid and carboxylic acids such as trifluoroacetic acid, trichloroacetic acid, dichloroacetic acid, difluoroacetic acid, tartaric acid and 2,5-dihydroxybenzoic acid. Trifluoroacetic acid and p-toluenesulfonic acid comprise a preferred class of acids whose anions are suitable in the process of the present invention, particularly trifluoroacetic acid. The anion is employed in a quantity from about 0.5 equivalent to about 200 equivalents per gram-atom of palladium (as the compound), preferably from about 1 equivalent to about 100 equivalents of the anion per gram atom of palladium.

The anion is preferably provided as the acid but in alternate modifications the anion is provided in the form of a salt. When a salt is employed to provide the anion, non-noble transition metal salts, i.e., salts of metals of Groups IIIB–VIIB of the Periodic Table of Elements, are usefully employed. Particularly suitable salts include those salts of copper, zirconium and vanadium. In the modifications where the anion is provided as a non-noble transition metal salt, copper salts are preferred. In yet another modification, it is suitable to provide the palladium and the anion as a single compound, e.g., the palladium p-toluenesulfonate acetonitrile complex formed by reacting palladium chloride with silver p-toluenesulfonate in acetonitrile.

The bidentate phosphorus ligand employed as precursor of the catalyst composition of the invention is a 1,3-bis(diarylphosphino)propane wherein the propane moiety is substituted in the 2 position with two hydrocarbyl substituents. A preferred class of such bidentate phosphorus ligands are represented by the formula:

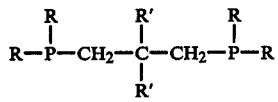

wherein R independently is monovalent aryl of from 6 to 20 carbon atoms inclusive and is a hydrocarbyl aryl group or is a substituted hydrocarbyl group wherein any non-hydrocarbyl substituents are polar substituents, particular alkoxy. Illustrative of suitable R groups are phenyl, naphthyl, tolyl, 2,4-dimethylphenyl, 2-methoxyphenyl, 2-ethoxynaphthyl, 3-propoxyphenyl, 2-methyl-4-methoxyphenyl, 2,4-dimethoxyphenyl and 2-propoxyphenyl. R' independently is a hydrocarbyl group of up to 10 carbon atoms and is an alkyl group such as methyl, ethyl, hexyl or decyl, or is aryl including alkaryl such as phenyl, naphthyl, tolyl or xylyl. Preferred R' groups are alkyl, particularly methyl. The R groups are the same or are different but preferably are the same. For best results at least one but preferably each R group is phenyl substituted with a polar substituent, particularly alkoxy, in a position ortho to the phosphorus, i.e., a 2-alkoxyphenyl substituent. illustrative of suitable bidentate phosphorus ligands are 2,2-dimethyl-1,3-bis[di(2-methoxyphenyl)phosphino]propane; 2,2-dimethyl-1,3-hydrocarbon. bis(diphenylphosphino)propane; 2-methyl-2-phenyl-1,3-bis(diphenylphosphino)propane; 2,2-diethyl-1,3-bis[di(2-methoxy-4-methylphenyl)phosphino]propane; 2,2-dipropyl-1,3-bis[di(4-methylphenyl)phosphino]propane and 2-methyl-2-butyl-1-(2-methoxyphenyl)-3-(2,6-diethoxyphenyl)propane. The class of 2,2-dimethyl-bis(phosphino)propanes are preferred and particularly preferred is 2,2-dimethyl-1,3-his[di(2-methoxyphenyl)phosphino]propane. The bidentate phosphorus ligands are suitably employed in a quantity of from about 0.1 mol to about 3 mol per mol of palladium compound, preferably in a quantity from about 0.75 mol to about 2 mol of palladium compound.

The activity of the catalyst composition is enhanced on occasion by the additional incorporation into the catalyst composition of a quinone. A variety of quinones are suitably employed as optional catalyst composition enhancers, including benzoquinone, naphthoquinone and anthraquinone. In general, when a quinone is employed, 1,4-quinones are preferred and particularly preferred is 1,4-benzoquinone. The use of a quinone is not required, but when a quinone is employed quantities of quinone up to 1000 mol of quinone per gram atom of palladium are useful, particularly amounts of quinone from about 25 mol to about 250 mol per gram atom of palladium.

The polymerization process comprises contacting the catalyst composition with carbon monoxide and at least one ethylenically unsaturated hydrocarbon. Suitable ethylenically unsaturated hydrocarbons have up to 20 carbon atoms inclusive, preferably up to 10 carbon atoms, and are aliphatic including ethylene and other alpha-olefins such as propylene, butylene, isobutylene, 1-hexene, 1-octene and 1-dodecene, or are arylaliphatic having an aryl substituent on a carbon atom of the ethylenic unsaturation, e.g., styrene, m-propylstyrene, p-methylstyrene and p-ethylstyrene. The members of the class of alpha-olefins are preferred as precursors of the linear alternating polymers. Preferred polymers are copolymers of carbon monoxide and ethylene or terpolymers of carbon monoxide, ethylene and propylene.

The polymers of the invention are linear alternating polymers having substantially one mole of carbon monoxide for each mole of When copolymers are desired, the total quantity of hydrocarbon will consist of a single ethylenically unsaturated hydrocarbon but when terpolymers are desired, the molar ratio of a first hydrocarbon, preferably ethylene, to the second hydrocarbon will be from about 1:1 to about 400:1, preferably from about 10:1 to about 100:1.

The catalyst composition is provided in a catalytic quantity. Suitable quantities of catalyst composition are those which provide from about $1 \times 10^{-7}$ to about $1 \times 10^{-3}$ gram atom of palladium per mol of ethylenically unsaturated hydrocarbon, preferably from about $1 \times 10^{-6}$ to about $1 \times 10^{-4}$ gram atom of palladium per mole of unsaturated hydrocarbon. The molar ratio of ethylenically unsaturated hydrocarbon to carbon monoxide is from about 10:1 to about 1.5, preferably from about 5:1 to about 1:2.

Polymerization is conducted under polymerization conditions in the liquid phase in the presence of an inert reaction diluent such as a lower alkanol, e.g., methanol or ethanol. The method of contacting the reactants and the catalyst composition is not critical and contact is maintained by conventional methods such as stirring or shaking. Typical reaction temperatures are from about 20° C. to about 200° C. and preferably are from about 30° C. to 150° C. Typical reaction pressures are from about 1 bar to about 200 bar, but more often are from about 20 bar to about 100 bar. Subsequent to reaction, the polymer product is recovered by conventional methods such as filtration or decantation. The polymer product will on occasion contain residues of the catalyst composition which are removed, if desired, by treatment with a solvent or a complexing agent which is selective for the residues.

Of particular interest are the polymers having a molecular weight from about 1,000 to about 200,000, but preferably from about 10,000 to about 50,000. Such polymers typically have a melting point from about 175° C. to about 300° C. and a limiting viscosity number (LVN), measured in a standard capillary viscosity measuring device in m-cresol at 60° C., of from about 0.5 to about 10.

The polymer products are known materials of established utility as premium thermoplastics. By way of illustration, the polymers are processed by known methods such as extrusion or injection molding into sheets, films, plates and shaped articles which are useful in the packaging industry and in the production of containers such as for food and drink. The polymers find additional application in the production of both internal and external parts for automotive applications.

The invention is further illustrated by the following Comparative Examples (not of the invention) and the following Illustrative Embodiments. In each of the Comparative Examples and Illustrative Embodiments, the copolymer products had a melting point of 257° C. For each of the copolymers, the $^{13}$C-NMR analysis was consistent with a linear alternating structure and confirmed that the copolymer comprised units of the repeating formula —CO—(CH$_2$—CH$_2$)—.

COMPARATIVE EXAMPLE I

A carbon monoxide/ethylene copolymer was produced by the following procedure. A mechanically stirred autoclave was charged with 200 ml of methanol. The air present in the autoclave was expelled by three times pressurizing the autoclave with carbon monoxide to a pressure of 50 bar and then releasing the pressure. The contents of the autoclave were brought to 65° C. and an equimolar mixture of carbon monoxide and ethylene was introduced until a pressure of 55 bar was reached. A catalyst solution was then introduced into the autoclave which consisted of 6 ml of methanol, 0.02 mmol of palladium acetate, 0.04 mmol of p-toluenesulfonic acid and 0.02 mmol of 1,3-bis(diphenylphosphino)propane. The pressure was maintained at 55 bar by continuing addition of the equimolar carbon monoxide/ethylene mixture. After 3 hours, the polymerization was terminated by cooling the reactor to ambient temperature and releasing the pressure. The polymer product was recovered by filtration, washed with methanol and dried at 70° C.

The polymer product had an LVN of 1.0 dl/g and had been produced at the rate of 1.3 kg of copolymer/g palladium/hr.

COMPARATIVE EXAMPLE II

The procedure of Comparative Example I was repeated except that the reaction temperature was 85° C. instead of 65° C. The copolymer product had an LVN of 0.5 dl/g and was produced at a rate of 5.0 kg copolymer/g palladium/hr.

ILLUSTRATIVE EMBODIMENT I

The procedure of Comparative Example II was repeated except that 2,2-dimethyl-1,3-bis(diphenylphosphino)propane was used in place of 1,3-bis(diphenylphosphino)propane. The copolymer product had an LVN of 0.5 dl/g and was produced at the rate of 8.4 kg of copolymer/g palladium/hr.

COMPARATIVE EXAMPLE III

A copolymer of carbon monoxide and ethylene was produced by a procedure substantially like that of Comparative Example I except that
(1) the polymerization temperature was 96° C. instead of 65° C.,
(2) 0.04 mmol of trifluoroacetic acid was used instead of 0.04 mmol of p-toluenesulfonic acid,
(3) the phosphine ligand was 1,3-bis[phenyl(2-methoxyphenyl)phosphino]propane instead of 1,3-bis(diphenylphosphino)propane, and
(4) the catalyst composition additionally contained 4 mmol of 1,4-benzoquinone.

The copolymer product had an LVN of 0.7 dl/g and was produced at a polymerization rate of 3.5 kg of copolymer/g palladium/hr.

ILLUSTRATIVE EMBODIMENT II

A copolymer of carbon monoxide and ethylene was produced according to the procedure of Comparative Example III except that the phosphine ligand was 2,2-dimethyl-1,3-bis[phenyl(2-methoxyphenyl)phosphino]propane. The copolymer product had an LVN of 0.7 dl/g and was produced at a polymerization rate of 9.3 kg of copolymer/g palladium/hr.

COMPARATIVE EXAMPLE IV

A carbon monoixde/ethylene copolymer was produced by a procedure substantially like that of Comparative Example I, except that
(1) the polymerization temperature was 97° C. instead of 65° C.,
(2) 0.04 mmol of trifluoroacetic acid was used instead of the 0.04 mmol of p-toluenesulfonic acid,
(3) the phosphine ligand was 1,3-bis[di(2-methoxyphenyl)phosphino]propane instead of the 1,3-bis(diphenylphosphino)propane, and
(4) the catalyst composition additionally contained 4 mmol of 1,4-benzoquinone.

The polymer product had an LVN of 1.0 dl/g and was produced at polymerization rate of 12.2 g of copolymer/g palladium/hr.

ILLUSTRATIVE EMBODIMENT III

A copolymer of carbon monoxide and ethylene was produced by a procedure substantially similar to that of Comparative Example IV except that the phosphine ligand was 2,2-dimethyl-1,3-bis[di(2-methoxyphenyl)phosphino]propane.

The copolymer product had an LVN of 0.9 dl/g and was produced at a polymerization rate of 20.0 kg copolymer/g palladium/hr.

COMPARATIVE EXAMPLE V

Copolymer of carbon monoxide and ethylene was produced in three separate experiments wherein the phosphine ligand was varied but the procedure was otherwise like that of Comparative Example I except that the polymerization temperature was 85° C. instead of 65° C.

(a) When the phosphine ligand was 2,4-bis(diphenylphosphino)pentane, the polymer product had an LVN of 0.4 dl/g and was produced at a polymerization rate of 4.6 kg copolymer/g palladium/hr.

(b) When the phosphine ligand was 1,3-bis(diphenylphosphino)butane, the polymer product had an LVN of 0.4 dl/g and was produced at a polymerization rate of 2.9 kg copolymer/g palladium/hr.

(c) When the phosphine ligand was 2-(diphenylphosphinomethyl)-3-diphenyl phosphinopropane-1, the copolymer product had an LVN of 0.5 dl/g and was produced at a polymerization rate of 5.4 kg of copolymer/g palladium/hr.

What is claimed is:

1. A catalyst composition formed for a palladium salt, the anion of a non-hydrohalogenic acid having a pKa less than about 6 and a bidentate phosphorus ligand of the formula

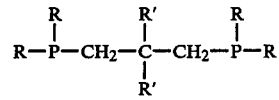

wherein R independently is a monovalent aryl group of from 6 to 20 carbon atoms inclusive or a monovalent alkoxy-substituted aryl group of from 6 to 20 carbon atoms inclusive and R, independently is a hydrocarbyl group of up to 10 carbon atoms.

2. The composition of claim 1 wherein each R' is alkyl.

3. The composition of claim 2 wherein each R is phenyl.

4. The composition of claim 3 wherein each R is 2-alkoxyphenyl.

5. The composition of claim 4 wherein each $R_1$ is methyl.

6. The Composition of claim 5 wherein each 2-alkoxyphenyl is 2-methoxyphenyl.

7. The composition of claim 1 wherein the palladium salt is palladium carboxylate, the anion is the anion of trifluoroacetic acid or p-toluenesulfonic acid, each $R_1$ is methyl and each R is 2-alkoxyphenyl.

8. The composition of claim 7 wherein the palladium carboxylate is palladium acetate, the anion is the anion of trifluoroacetic acid and each R is 2-methoxyphenyl.

* * * * *